US006664405B2

(12) United States Patent
Lee

(10) Patent No.: US 6,664,405 B2
(45) Date of Patent: Dec. 16, 2003

(54) METHOD FOR ISOLATING HIGH-PURIFIED UNSATURATED FATTY ACIDS USING CRYSTALLIZATION

(75) Inventor: Seong Kweon Lee, Namyangju (KR)

(73) Assignee: Lipozen, Inc., Gyeonggi-Do (KR)

( * ) Notice: Subject to any disclaimer, the term of this patent is extended or adjusted under 35 U.S.C. 154(b) by 0 days.

(21) Appl. No.: 09/996,544

(22) Filed: Nov. 28, 2001

(65) Prior Publication Data

US 2003/0027865 A1 Feb. 6, 2003

(30) Foreign Application Priority Data

Nov. 30, 2000 (KR) ........................................ 2000-71846

(51) Int. Cl.[7] ................................................ C07C 51/43
(52) U.S. Cl. ...................................................... 554/186
(58) Field of Search ......................................... 554/186

(56) References Cited

U.S. PATENT DOCUMENTS 5,550,156 A 8/1996 Kyle .......................... 514/547

FOREIGN PATENT DOCUMENTS

| | | |
|---|---|---|
| GB | 1240513 | 7/1971 |
| WO | 9212711 | 8/1992 |

OTHER PUBLICATIONS

AOAC Official Methods of Analysis, 28.059, p. 514, (1984).
Haagsma, N., et al. "Preparation of an w3 Fatty Acid Concentrate from Cod Liver Oil" JAOCS, vol. 59, No. 3, pp. 117–118, (1982).

*Primary Examiner*—Raymond Henley, III
(74) *Attorney, Agent, or Firm*—Ladas and Parry

(57) ABSTRACT

The present invention relates to a method for isolating and purifying only a certain unsaturated fatty acid in a high purity from fatty acids present in oils including vegetable oils and fish oils by means of crystallization. More particularly, the present invention relates to a method for isolating and purifying only the desired unsaturated fatty acid in a high purity from fatty acids present in oils by selectively using a urea-addition crystallization, and a cooling crystallization or a high liquid chromatography. Specifically, the present invention provides a method for isolating and purifying linoleic acid or oleic acid as unsaturated fatty acids, in a high purity of at least 99% by subjecting fatty acids derived from oils, particularly, a vegetable oil containing linoleic acid or oleic acid at a high concentration, such as safflower oil, corn germ oil or olive oil, as the raw material to two-step urea-addition crystallization using methanol and urea and then crystallizing the concentrated unsaturated fatty acid from an organic solvent under cooling at temperature of −5° C. to −10° C. without stirring, or a method for isolating eicosapentaenoic acid (EPA) as unsaturated fatty acid, in a high purity of at least 99% by subjecting fatty acids derived from oils, particularly, a fish oil containing EPA at a high concentration, such as sardine oil, as the raw material to two-step urea-addition crystallization using methanol and urea to obtain a concentrated unsaturated fatty acid having a high purity and then further purifying the high-purified, concentrated fatty acid by means of a high liquid chromatography using a column filled with Ag-silica or Ag-alumina.

6 Claims, 2 Drawing Sheets

METHOD FOR ISOLATING HIGH-PURIFIED UNSATURATED FATTY ACIDS USING CRYSTALLIZATION

TECHNICAL FIELD

The present invention relates to a method for isolating and purifying only a certain unsaturated fatty acid in a high purity from fatty acids present in oils including vegetable oils and fish oils by means of crystallization. More particularly, the present invention relates to a method for isolation and purifying only the desired unsaturated fatty acid in a high purity from fatty acids present in oils by selectively using urea-addition crystallization, and a cooling crystallization or a high liquid chromatography.

Specifically, the present invention provides a method for isolating and purifying linoleic acid or oleic acid as unsaturated fatty acids, in a high purity of at least 99% by subjecting fatty acids derived from oils, particularly, a vegetable oil containing linoleic acid or oleic acid at a high concentration, such as safflower oil, corn germ oil or olive oil, as the raw material to two-step urea-addition crystallization using methanol and urea and then crystallizing the concentrated unsaturated fatty acid from an organic solvent under cooling at temperature of −5° C. to ~−10° C. without stirring Further, the present invention provides a method for isolating and purifying eicosapentaenoic acid (EPA) as unsaturated fatty acid, in a high purity of at least 99% by subjecting fatty acids derived from oils, particularly, a fish oil containing EPA at a high concentration, such as sardine oil, as the raw material to two-step urea-addition crystallization using methanol and urea to obtain a concentrated unsaturated fatty acid having a high purity and then further purifying the high-purified, concentrated fatty acid by means of a high liquid chromatography using a column filled with Ag-silica or Ag-alumina.

BACKGROUND ART

Various animal and vegetable oils, for example, vegetable oils such as safflower oil, corn germ oil and olive oil and fish oils such as sardine oil contain much saturated and unsaturated fatty acids having valuable effects for the food and medicinal purpose. The fatty acids present in such animal and vegetable oils include saturated fatty acids such as palmitic acid, stearic acid, etc., and unsaturated fatty acids such as palmitoleic acid, oleic acid, linoleic acid, linolenic acid, gamm-linolenic acid, arachidonic acid, eicosapentaenoic acid (EPA), docosahexaenoic acid (DHA), etc.

Among fatty acids derived from such oils, particularly, unsaturated fatty acids have numerous effects useful for food and medicinal purposes and therefore, have been widely used in the field of food and pharmaceutical preparation. The fatty acids present in oils have the following physiological activities. Palmitoleic acid is used as the raw material for cosmetics and a skin protectant; and oleic acid has been known as the raw material for ointments, skin absorbefacient (patch, patch formulation for oral administration, etc.), triolein and synthetic phospholipids, medium for cell culture, etc. Linoleic acid is a source of essential fatty acids and the raw material for cosmetics (vitamin complex) and has an anti-inflammatory activity and an activity for preventing skin cornification; gamma-linolenic acid is a precursor of prostaglandin series 1 and has an effect of improving dermatopathy and an effect of preventing and treating arteriosclerosis and hypertension; and alpha-linolenic acid is a precursor for synthesis of EPA and has an effect of lowering blood cholesterol level and an effect of preventing cardiac disease and adult diseases. EPA has an effect of lowering blood cholesterol and triglyceride levels, inhibiting inflammation and preventing arteriosclerosis and is used as a precursor of prostaglandin series 3. DHA is a fatty acid for constitution of cerebral and ophthalmic cell membrane and has an effect of improving brain function and preventing and alleviating dementia and Alzheimer disease and is used as a precursor of prostaglandin series 3.

However, in order to use such unsaturated fatty acids as the raw material for food and pharmaceutical products they are in need of isolation and purification in a high purity.

For such a purpose numerous methods have been developed. As the method for isolating and purifying unsaturated fatty acids in the prior art, the urea-addition crystallization has been widely known. However, prior urea-addition crystallization could not control the behavior of urea molecular group, and therefore, has been used for the isolation in a mid purity rather than in a high purity. Therefore, when the isolation and purification in a high purity is required particularly for the purpose of medicinal use, there is an urgent need for the development of a novel technique different from the prior urea-addition crystallization technique.

With regard to the prior urea-addition crystallization, the alcoholic -liquid cooling method for simultaneously dissolving fatty acids and urea has been reported in numerous references (e.g. U.S Pat. No. 1,240,513; JAOCS, 59,117~118(March 1982), Haagsma). However, such cooling method could not control the size of urea molecular group, and therefore, has some disadvantages in that urea and urea inclusion compound are simultaneously precipitated in the form of a crystal when the reaction mixture is cooled, and thus, the utility of urea is greatly decreased to the extent that undesirable fatty acids cannot be removed, In order to make up such disadvantages, the necessity for significantly lowering the cooling rate has been raised when the reaction mixture is cooled.

However, the method wherein the cooling rate is lowered as above also has some disadvantages in that the production time is very slow, and further, due to a long stay of unsaturated fatty acids at high temperature the acidification is rapidly proceeded to lower the oxidation stability of fatty acids, so that such method cannot be utilized in a mass-scale production.

Therefore, the necessity for a method for selectively isolating and purifying only the desired unsaturated fatty acid in a high purity from the fatty acid mixture derived from animal and vegetable oils with overcoming the disadvantages involved in the prior methods has been urgently raised. Thus, the present inventors have combined numerous techniques for isolation and purification in a various manner and then assayed the effect of such combined method, As a result, we have identified that the desired unsaturated fatty acids such as linoleic acid, oleic acid or EPA can be isolated in a high purity by conducting the urea-addition crystallization in two steps and then selectively utilizing the cooling crystallization or the high liquid chromatography, as specifically stated below, and then completed the present invention.

That is, in consideration of the fact that by controlling the behavior of the urea molecular group the urea inclusion compound of the desired fatty acids can be perfectly formed even at an high cooling rate without precipitation of urea crystals, the present invention adopts the molecular encapsulation technique, which allows the fatty acids present in the urea inclusion compound to minimally contact with the air, to optionally control the behavior of urea molecular group so that the stability of unsaturated fatty acids can be increased and the selectivity of fatty acids isolation can also be greatly increased to isolate and purify the desired fatty acids in a high purity.

Therefore, the present invention provides a method for isolating and purifying the unsaturated fatty acids very useful for human being, which are a source of energy and further constitute the biological lipids in cell membranes such as vitamins, hormones, etc., by means of a urea-addition crystallization, and then a cooling crystallization or a high liquid chromatography column.

SUMMARY OF THE INVENTION

The purpose of the present invention is to provide a method for isolating and purifying unsaturated fatty acids in a high purity of at least 99% by subjecting fatty acids derived from vegetable oils containing linoleic acid or oleic acid at a high concentration or fish oils such as sardine oil containing EPA at a high concentration, as the raw material to two-step urea-addition crystallization or high liquid chromatography.

Another purpose of the present invention is to provide a method for isolating and purifying linoleic acid or oleic acid as unsaturated fatty acids, in a high purity of at least 99% by subjecting fatty acids derived from oils, particularly, a vegetable oil containing linoleic acid or oleic at a high concentration, such as safflower oil, corn germ oil or olive oil, as the raw material to two-step urea-addition crystallization using methanol and urea and then crystallizing the concentrated unsaturated fatty acid from an organic solvent under cooling temperature of −5° C. to −10° C. without stirring.

Still another purpose of the present invention provides a method for isolating and purifying EPA as unsaturated fatty acid, in a high purity of at least 99% by subjecting fatty acids derived from oils, particularly a fish oil containing EPA at a high concentration, such as sardine oil, as the raw material to two-step urea-addition crystallization using methanol and urea to obtain a concentrated unsaturated fatty acid having a high purity and then further purifying the high-purified, concentrated fatty acid by means of a high liquid chromatography using a column filled with Ag-silica or Ag-alumina.

BRIEF DESCRIPTION OF DRAWINGS

For a thorough understanding of the nature and purposes of the present invention, reference should be made to the following detailed description taken in connection with the accompanying drawing in which.

DETAILED DESCRIPTION OF THE INVENTION

Figure 1:
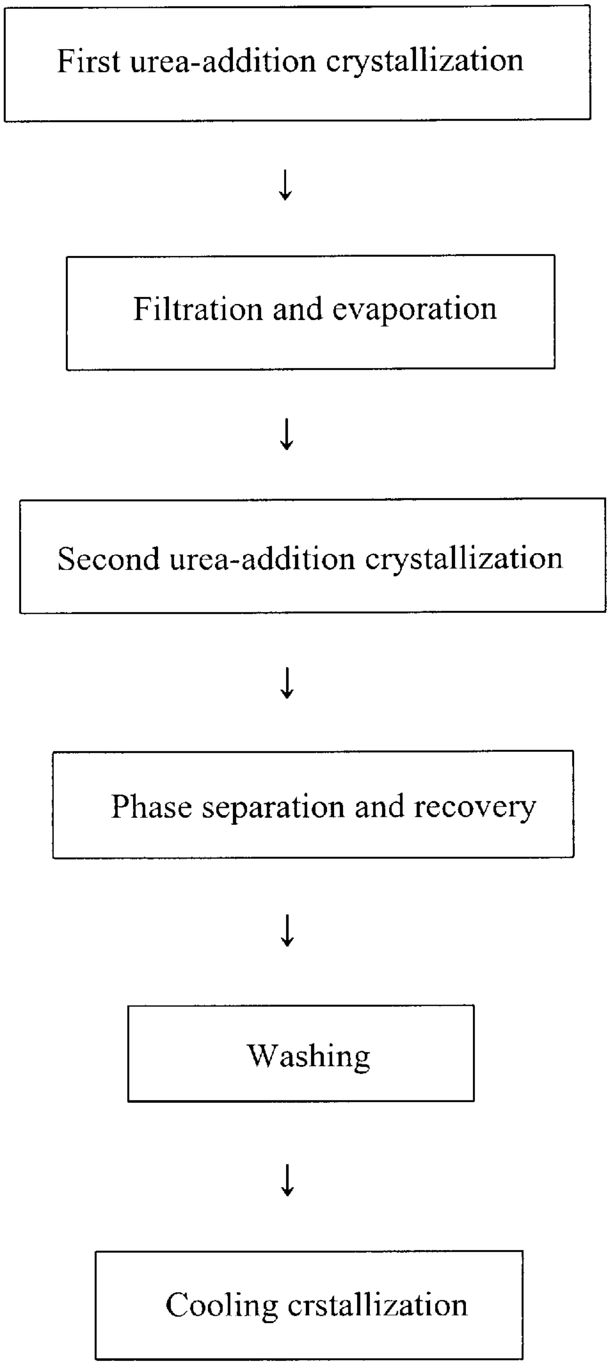
FIG. 1 is a flow chart showing the method for isolating and purifying linoleic acid and oleic acid in a high purity according to the present invention and FIG. 2 is a flow chart schematically showing the method for isolating and purifying eicosapentaenoic acid (EPA) in a high purity according to the present invention.

Hereinafter, the present invention will be more specifically explained with reference to the drawing ad attached.

FIG. 1 is the flow chart schematically showing the method for isolating and purifying linoleic acid and oleic acid, which are contained particularly in vegetable oils in a high concentration, in a high purity according to the present invention.

According to the present invention, linoleic acid and oleic acid can be isolated and purified in a high purity of at least 99% by subjecting fatty acids derived from vegetable oils containing linoleic acid or oleic acid at a high concentration, such as safflower oil, corn germ oil or olive oil, as the raw material to two-step urea-addition crystallization using methanol and urea and then crystallizing the concentrated unsaturated fatty acid from an organic solvent under cooling temperature of −5° C. to −10° C. with stirring. With reference to FIG. 1, the method for isolating and purifying linoleic acid and oleic acid according to the present invention is composed of the steps specifically illustrated below:

(1) Step of the first urea-addition crystallization wherein urea is added to methanol in the weight ratio of methanol: urea=2.5~3.5:1~2 and completely dissolved at elevated temperature of 65° C. to 75° C., and then the fatty acids derived from vegetable oils are injected in incremental portions into the resulting urea solution and cooled to room temperature at the rate of 0.2° C.~0.5° C./min.;

(2) After the step of the urea-addition crystallization, the step of removing the saturated and unsaturated fatty acids in the form of urea inclusion compound (UIC) by filtration under reduced pressure;

(3) Step of evaporating the filtrate containing the unsaturated fatty acid thus obtained using a vacuum rotary evaporator to remove the residual methanol thereby obtaining the solid product;

(4) Step of adding water and a small amount of hydrochloric acid to the solid product and then stirring the mixture to remove any trace amount of the residual urea and methanol in the solid product thereby recovering the upper layer containing the unsaturated fatty acid;

(5) Step of the second urea-addition crystallization wherein urea is added to methanol in the weight ratio of methanol: urea=2.5~3.5:1.2 and completely dissolved at elevated temperature of 65° C. to 75° C., and then the fatty acids separated from the step (4) are injected in incremental portions over 5 to 8 steps into the resulting urea solution and cooled to room temperature at the rate of 2.5 ° C.~0.5° C./min.;

(6) Step of filtering the mixture under reduced pressure to remove the filtrate containing impurities and recover the concentrated unsaturated fatty acid (97~98%) as the urea inclusion compound(UIC) in the form of a solid particle;

(7) Step of adding water and hexane to the unsaturated fatty acid thus recovered in the form of a solid particle and then adding a small amount of hydrochloric acid to cause the phase separation of urea and concentrated linoleic acid thereby recovering linoleic acid or oleic acid having a high purity as the upper layer;

(8) Step of washing the resulting concentrated linoleic acid or oleic acid 2 to 3 times with water and then removing hexane using a rotary evaporator to obtain linoleic acid or oleic acid having a high purity at least 98%; and (9) Step of adding an organic solvent to completely dissolve the unsaturated fatty acid obtained in the step (8) and then cooling the solution to −5° C. to −10° C. without stirring to crystallize the desired unsaturated fatty acid, thereby further purifying the unsaturated fatty acid having a high purity obtained in the step (8).

Figure 2:
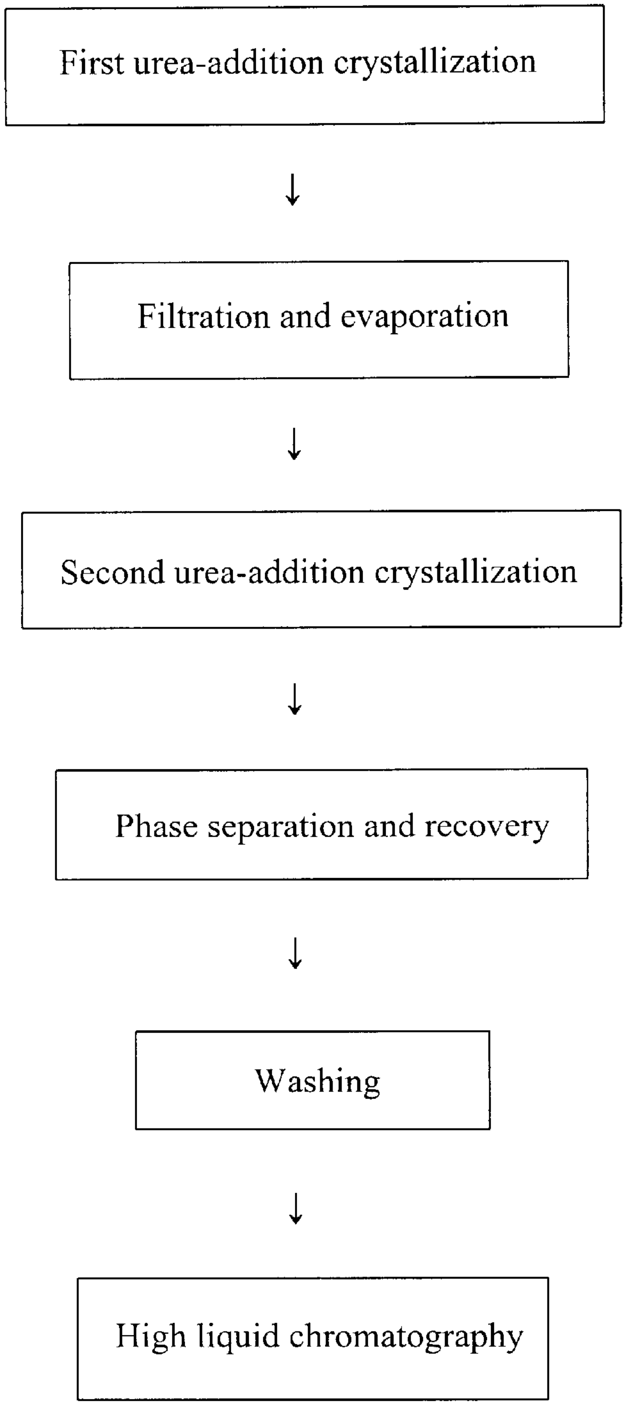

FIG. 2 is a flow chart schematically showing the method for isolating and purifying EPA, which is the unsaturated fatty acid contained particularly in fish oils in a high concentration, in a high purity according to the present invention.

According to the present invention, EPA can be isolated and purified in a high purity of at least 99% by subjecting fatty acids derived from fish oils containing EPA at a high concentration, such as sardine oil, as the raw material to two-step urea-addition crystallization using methanol to recover the concentrated unsaturated fatty acid having a high purity and then subjecting the obtained concentrated unsaturated fatty acid having a high purity to high liquid chromatography column filled with Ag-silica or Ag-alumina. With reference to FIG. 2, the method for isolating and purifying EPA according to the present invention is composed of the steps specifically illustrated below:

(1) Step of the first urea-addition crystallization wherein urea is added to methanol in the weight ratio of methanol: urea=2.5–3.5:1.2 and completely dissolved at elevated temperature of 65° C. to 75° C., and then the fatty acids derived from fish oils are injected in incremental portions into resulting urea solution and cooled to room temperature at the rate of 0.2° C.~0.5° C./min.;

(2) After the step of the first urea-addition crystallization, the step of removing the saturated and unsaturated fatty acids in the form of urea inclusion compound (UIC) by filtration under reduced pressure;

(3) Step of evaporating the filtrate containing the unsaturated fatty acid thus obtained using a vacuum rotary evaporator to remove the residual methanol thereby obtaining the solid product;

(4) Step of adding water and a small amount of hydrochloric acid to the solid product and then stirring the mixture to remove any trace amount of the residual urea and methanol in the solid product thereby recovering the upper layer containing the unsaturated fatty acid;

(5) Step of the second urea-addition crystallization wherein urea is added to methanol in the weight ratio of methanol: urea=2.5~3.2 :1~2 and completely dissolved at elevated temperature of 65° C. to 75° C. , and then the fatty acids separated from the step (4) are injected in incremental portions over 5 to 8 steps into the resulting urea solution and cooled to room temperature at the rate of 0.2~0.5 /mm;

(6) Step of filtering the mixture under reduced pressure to remove the filtrate containing impurities and recover the concentrated EPA as the urea inclusion compound in the form of a solid particle;

(7) Step of adding water and hexane to the unsaturated fatty acid thus recovered in the form of a solid particle and then adding a small amount of hydrochloric acid to cause the phase separation of urea and concentrated EPA thereby recovering EPA having a high purity as the upper layer;

(8) Step of washing the resulting concentrated EPA 2 to 3 times with water and then removing hexane using a rotary evaporator to obtain EPA having a high purity; and (9) Step of passing EPA obtained in the step (8) through a high liquid chromatography column filled with Ag-silica or Ag-alumina to isolate and purify EPA, thereby further purifying EPA having a high purity obtained in the step (8).

As the raw materials from which the fatty acids used in said method according to the present invention are derived, any of vegetable oils containing oleic acid, linoleic acid and gamma-linolenic acid, etc. at a high concentration and fish oils containing EPA at a high concentration can be used, and particularly safflower oil, olive oil, corn germ oil, sardine oil, etc. is preferably used. The raw materials as above are commonly converted into the fatty acids according to the conventional method such as AOAC method and then used in the method of the present invention. The unsaturated fatty acid having a high purity as finally obtained according to the method of the present invention is characteristically linoleic acid, oleic acid or EPA having a purity of at least 99%.

The fatty acids derived from oils used in the present invention are not injected into the reaction system at once but introduced in incremental portions over 5 to 8 steps. Such a manner of introduction is to control the behavior of urea molecular group so that the lowering of urea utility due to the precipitation of urea crystals is prevented and further the retention time at high temperature is decreased to improve the oxidation stability of the resulting product.

In isolating and purifying the unsaturated fatty acids in a high purity according to the present invention, after urea is added to methanol, the mixture is completely dissolved at elevated temperature of 65~75° C. and then the fatty acids are added in incremental portions over 5 to 8 steps then mixture is cooled at a high cooling rate of 0.2~0.5 /mm to form the non-equilibrium cooling state. In cooling under the equilibrium state, a difference in the crystallizing temperature of urea and the urea molecular group as the urea inclusion compound is about 4~5, and therefore, it cannot help avoiding the crystallization of urea. However, when the fatty acids are added in several portions according to the present invention, the formation of urea molecular group can be controlled so that substantially a total amount of fatty acid can form the urea inclusion compound at a high cooling rate. Therefore, by utilizing such a incremental injecting method, the amount of urea in the urea and methanol mixture according to the prior method is decreased and the sections of cooling temperature ranges for urea and urea inclusion compound are separated from each other so that only the desired fatty acid can be converted into form of urea inclusion compound.

To isolate linoleic acid or oleic acid the fatty acids derived from vegetable oils are used as the raw material to conduct the first urea-addition crystallization thereby precipitating the saturated fatty acids including palmitic acid, stearic acid and most of oleic acid in the form of urea inclusion compound. The urea inclusion compound thus precipitated is removed by filtration in the step (2) to separate the filtrate containing a small amount of urea and unsaturated fatty acids including linoleic acid and alpha-linolenic acid. Meanwhile, after the second urea-addition crystallization in the step (5), the filtrate containing the residual urea, which remained after being used in the reaction, and impurities such as alpha-linoleic acid, are removed.

In the cooling crystallization as the final step (9) for isolating and purifying linoleic acid or oleic acid from the fatty acids of vegetable oils, it is important that the organic solvent added to isolate and purify only the desired unsaturated fatty acid having a high purity in the form of urea inclusion compound is added in the ratio of 1:1~4 with respect to the unsaturated fatty acid on the basis of weight. As the organic solvent for such purpose, hexane or heptane can be preferably used.

The method for isolating and purifying EPA in a high purity from the fatty acids for fish oils according to the present invention is characterized in that the unsaturated fatty acid is concentrated by means of high liquid chromatography column filled with Ag- silica or Ag-alumina.

Thus, the present invention can allow the mass-scale production and induce high oxidation stability due to shortening of the process time.

The present invention is more specifically explained by the following references and examples. However, it will be apparent to a person having an ordinary knowledge in the relevant technical field that these examples are provided only for illustration of the present invention but not intended to limit the scope of the present invention in any manner.

Reference 1: Conversion of Triglycerides into Fatty Acids

The conversion of triglycerides into fatty acids was conducted on the basis of AOAC method. First, NaOH (480 g) and $Na_2$ EDTA (5 g)were dissolved in the mixed solution of water (1.6 l) and ethanol (1.6 l) at 60° C. , and then triglycerides (1 kg) were added to induce saponification for 30 minutes. Then, hexane (7 l)and water (0.8 l) were injected into the mixture, stirred for one (1) hour and then allowed to stand. The unsaponificated material of the upper layer was removed and then, the pH value was adjusted to 1 by adding concentrated hydrochloric acid to the solution of the lower layer and then the fatty acid layer of the upper layer was recovered and then evaporated with a vacuum rotary evaporator to remove hexane.

Reference 2: Analysis of Fatty Acid Composition

The fatty acids were converted into methyl ester of fatty acids according to AOAC method (see, "Preparation of an ω3 Fatty acid concentrate from cod liver oil", JAOCS, Vol. 59, No. 3, March 1982, pp 117~183) in order to analyze the composition of fatty acids. For such purpose, HP5890 series II of Hewlett Packard was used as the gas chromatography analyzer and FID of Hewlett Packard was used as the detector. The column used in this analysis was Supelcowax made by Hewlett Packard and the temperature at the time of analysis was elevated from 175° C. to 240° C. at the rate of 2.5° C./min. The temperature of the injector was 250° C. and the temperature of the detector was 260° C.

Reference 3: Preparation of the Filler (Ag-silica, Ag-alumina) for High Liquid Chromatography 20 g of silver nitrate ($AgNO_3$) powder was added to the boiling water and then completely dissolved with stirring. Then, 200 g of silica powder was added to the resulting solution, stirred for 1~2 hours and then dried at temperature of 100~120° C. to prepare Ag-silica filler in the form of a powder.

Ag-alumina filler was prepared according to the same procedure as above only except that alumina powder is used instead of silica powder.

EXAMPLE 1

Isolation and Purification of Linoleic Acid in a High Purity 1.5 kg of urea was added to 4 l of methanol and then completely dissolved at elevated temperature of 70° C. Then, 1 kg of the fatty acids (composition: palmitic acid 8 wt %, stearic acid 1.7 wt %, oleic acid 15 wt %, linoleic acid 75 wt %, alpha-linolenic acid 0.3 wt %) derived from safflower oil as converted according to the method of Reference 1 was added to the resulting urea solution in incremental portions over 6 steps and cooled to room temperature at the cooling rate of0.2° C./min. The resulting reaction mixture was filtered to remove saturated fatty acids including palmitic acid and stearic acid and most of oleic acid in the form of urea inclusion compound and the filtrate containing a small amount of urea and unsaturated fatty acids including linoleic acid and alpha-linolenic acid was separated. The separated filtrate was evaporated using a vacuum rotary evaporator to remove the residual methanol thereby obtaining the solid product. In order to remove any trace amount of urea and methanol present in the solid product, 1 l of water and a small amount of hydrochloric acid were added to the solid product and the mixture was stirred. Then, the upper layer of unsaturated fatty acids was recovered. Subsequently, 1.5 kg of urea was added to 4 l of methanol and then completely dissolved at elevated temperature of 70° C. Then, the unsaturated fatty acid obtained above was added to the resulting urea solution in incremental portions over 6 steps and cooled to room temperature at the cooling rate of 0.2° C./min. The reaction mixture was then filtered under reduced pressure to recover the concentrated linoleic acid (97–98%) in the form of solid urea inclusion compound while removing the filtrate containing alpha-linolenic acid as the main component. Water (2 l) and hexane (2 l) were added to high-purified linoleic acid thus obtained in the form of a solid particle followed by addition of a small amount of hydrochloric acid to cause the phase separation of urea and concentrated linoleic acid. The upper layer of linoleic acid having a high purity was recovered. Concentrated linoleic acid present in the dissolved state in hexane was washed three times with water, evaporated using a rotary evaporator to remove hexane thereby obtaining high-purified linoleic acid (purity: 98%).

Thereafter, for further purification 700 g of high-purified linoleic acid obtained above was completely dissolved in 700 ml of hexane and then crystallized by cooling to −5° C. to −10° C. without stirring. The resulting crystals in the form of a solid were filtered and then evaporated to remove hexane thereby obtaining 630 g of high-purified linoleic acid in a yield of 84% and a purity of 99.8%. High-purified linoleic acid obtained according to the above method was analyzed according to the method of Reference 2. The result of analysis can be seen in the following Table 1.

EXAMPLE 2

Isolation and Purification of Oleic Acid in a High Purity 1.5 kg of urea was added to 4 l of methanol and then completely dissolved at elevated temperature of 75° C. Then, 1 kg of the fatty acids (composition: palmitic acid 12 wt %, palmitooleic acid 2 wt %, stearic acid 4 wt %, oleic acid 70 wt %, linoleic acid 12 wt %) derived from olive oil as converted according to the method of Reference 1 was added to the resulting urea solution in incremental portions over 7 steps and cooled to room temperature at the cooling rate of 0.3° C./min. The resulting reaction mixture was filtered under reduced pressure, and the filtrate was evaporated using a vacuum rotary evaporator to remove the residual methanol thereby obtaining the solid product. In order to remove any trace amount of urea and methanol present in the solid product, 2 l of water and a small amount of hydrochloric acid were added to the solid product and the mixture was stirred. Then, the upper layer of unsaturated fatty acids was recovered. Subsequently, 2 kg of urea was again added to 6 l of methanol and then completely dissolved at elevated temperature of 70° C. Then, the unsaturated fatty acid obtained above was added to the resulting urea solution in incremental portions over 6 steps and cooled to room temperature at the cooling rate of 0.2° C./min. The reaction mixture was then filtered under reduced pressure to recover the solid particles to which water(2 l) and hexane(2 l) were added and then a small amount of hydrochloric acid was added to cause the phase separation of urea and concentrated oleic acid. The upper layer of oleic acid having a high purity was recovered. The separated upper hexane layer was washed two to three times with water, evaporated using a rotary evaporator to remove hexane thereby obtaining 680 g of high-purified oleic acid.

Thereafter, for further purification 680 g of high-purified oleic acid obtained above was completely dissolved in 700 ml of hexane and then crystallized by cooling to −5° C. to −10° C. without stirring. The resulting crystals were filtered and then evaporated to remove hexane thereby obtaining 609 g of high-purified linoleic acid in a yield of 87% and a purity of 99.7%.

High-purified oleic acid obtained according to the above method was analyzed according to the method of Reference 2. The result of analysis can be seen in the following Table 1.

EXAMPLE 3

Isolation and Purification of EPA in a High Purity 4 kg of urea was added to 12 l of methanol and then completely dissolved at elevated temperature of 70° C. Then, 1 kg of the fatty acids (composition: myristic acid 7 wt %, palmitic acid 18 wt %, palmitooleic acid 10 wt %, stearic acid 3 wt %, oleic acid 14 wt %, linoleic acid 2 wt %, steadonic acid 2.5 wt %, EPA 18 wt %, DHA 10 wt %, others 15.5 wt %) derived from sardine oil as converted according to the method of Reference 1 was added to the resulting urea solution in portions over 6 times, cooled to room temperature at the cooling rate of 0.3° C./min. and then filtered under reduced pressure. The filtrate was evaporated using a vacuum rotary evaporator to remove the residual methanol thereby obtaining the solid product. Then, 2 l of water and a small amount of hydrochloric acid were added to the solid product and the mixture was stirred. Then, the upper layer of unsaturated fatty acids was recovered. Subsequently, 1.5 kg of urea was added again to 4.5 l of methanol and then completely dissolved at elevated temperature of 70° C. Then, the unsaturated fatty acid recovered above was added to the resulting urea solution in portions over 6 times and cooled to room temperature at the cooling rate of 0.2° C./min. The reaction mixture was then filtered under reduced pressure to recover EPA in the form of a solid particle while removing the filtrate. Water (2 l) and hexane (2 l) were added to the separated solid particles and then a small amount of hydrochloric acid was added to cause the phase separation. The upper layer of concentrated EPA was recovered. The upper hexane layer thus separated was washed two to three times with water, evaporated using a rotary evaporator to remove hexane thereby obtaining concentrated EPA.

Thereafter, concentrated EPA obtained above was fractionated through high liquid chromatography column filled with Ag-silica prepared according to the method of Reference 3. Fractionation was conducted in the manner that Ag-silica was filled with 150 g of Ag-silica filler and about 50 g of the concentrated EPA was dissolved in 2 l of hexane and then isolated and purified by passing through the column along with 5% ether. Hexane was removed from the fractionated liquid layer to obtain 108 g of high-purified EPA in a yield of 60% and a purity of 99.2%. High-purified EPA obtained according to the above method was analyzed according to the method of Reference 2. The result of analysis can be seen in the following Table 1.

TABLE I

Analysis of the composition of high-purified unsaturated fatty acids obtained from Examples 1 to 3

| | Example | | |
|---|---|---|---|
| Composition | Example 1 | Example 2 | Example 3 |
| Palmitic acid (GC area %) | | 0.1 | |
| Palmitooleic acid (GC area %) | | 0.1 | |
| Oleic acid (GC area %) | 0.1 | 99.7 | |
| Lonoleic acid (GC area %) | 99.8 | 0.1 | |
| Alpha-linoleic acid (GC area %) | 0.1 | | |
| EPA (GC area %) | | | 99.2 |
| DHA (GC area %) | | | 0.5 |
| Others (GC area %) | | | 0.3 |
| Total (GC area %) | 100 | 100 | 100 |
| Acidity | 199.9 | 197.4 | 187.5 |
| Peroxide value | 3.4 | 3.1 | 3.1 |
| Water content (%) | 0.07 | 0.05 | 0.06 |
| Yield (%) | 84 | 87 | 60 |

The present invention develops the novel method for controlling the behavior of urea molecular group. That is, in consideration of the fact that by controlling the behavior of the urea molecular group the urea inclusion compound of the desired fatty acids can be perfectly formed even at a high cooling rate without precipitation of urea crystals, the present invention adopts the molecular encapsulation technique, which allows the fatty acids present in the urea inclusion compound to minimally contact with the air, to optionally control the behavior of urea molecular group so that the stability of unsaturated fatty acids can be increased and the selectivity of fatty acid isolation can also be greatly increased to isolate and purify the desired fatty acids in a high purity.

What is claimed is:

1. A method for isolating and purifying an unsaturated fatty acid to a high purity which comprises subjecting fatty acids derived from vegetable oils to a two-step urea-addition crystallization using methanol and urea to recover the concentrated unsaturated fatty acids in a high purity, and crystallizing said unsaturated fatty acid from a solution with an organic solvent under cooling at a temperature of −5° C. to −10° C. without stirring to isolate and purify linoleic acid or oleic acid.

2. The method according to claim 1 wherein linoleic acid or oleic acid is isolated and purified in a purity of at least 99% by a process comprising:

(1) a step of the first urea-addition crystallization wherein urea is added to methanol in the weight ratio of methanol: urea=2.5~3.2:1~2 and completely dissolved at elevated temperature of 65° C. to 75° C., and then the fatty acids derived from vegetable oils are injected in incremental portions into the resulting urea solution and cooled to room temperature at the rate of 0.2° C.~0.5° C./min.;

(2) after the step of the first urea-addition crystallization, the step of removing the saturated and unsaturated fatty acids in the form of urea inclusion compound by filtration under reduced pressure;

(3) step of evaporation the filtrate containing the unsaturated fatty acid thus obtained using a vacuum rotary evaporator to remove the residual methanol thereby obtaining the solid product;

(4) step of adding water and a small amount of hydrochloric acid to the solid product and then stirring the mixture to remove any trace amount of the residual urea and methanol in the solid product thereby recovering the upper layer containing the unsaturated fatty acid;

(5) step of the second urea-addition crystallization wherein urea is added to methanol in the weight ratio of methanol: urea=2.5~3.2:1~2 and completely dissolved at elevated temperature of 65° C., to 75° C., and then the fatty acids separated from the step (4) are injected in incremental portions over 5 to 8 steps into the resulting urea solution and cooled to room temperature at the rate of 0.2° C.~0.50° C./min.;

(6) step of filtering the mixture under reduced pressure to remove the filtrate containing impurities and recover the concentrated unsaturated fatty acid (97–98%) as the urea inclusion compound in the form of a solid particle;

(7) step of adding water and hexane to the unsaturated fatty acid thus recovered in the form of a solid particle and then adding a small amount of hydrochloric acid to cause the phase separation of urea and concentrated linoleic acid or oleic acid thereby recovering linoleic acid or oleic acid having a high purity as the upper layer;

(8) step of washing the resulting concentrated linoleic acid or oleic acid 2 to 3 times with water and then removing hexane using a rotary evaporator to obtain linoleic acid or oleic acid having a high purity; and (9) step of adding an organic solvent to completely dissolve the unsaturated fatty acid obtained in the step (8) and then cooling the solution to −5° C. to −10° C. without stirring to crystallize the desired unsaturated fatty acid.

3. The method according to claim 2, wherein in the step (9) the organic solvent is added to the unsaturated fatty acid in the ratio of 1:1~4 by weight.

4. The method according to claim 3, wherein the organic solvent is hexane or heptane.

5. A method for isolating and purifying an unsaturated fatty acid to a high purity which comprises subjecting fatty acids derived from fish oils to a two-step urea-addition crystallization using methanol and urea to recover the concentrated unsaturated fatty acids in a high purity, and passing said unsaturated fatty acids through a high liquid chromatography column filled with Ag-silica or Ag-alumina to isolate and purify EPA in a high purity.

6. The method according to claim 5 wherein EPA is isolated and purified in a purity of at least 99% by a process comprising:

(1) step of the first urea-addition crystallization wherein urea is added to methanol in the weight ratio of methanol: urea=2.5~3.5:1~2 and completely dissolved at elevated temperature of 65 to 75, and then the fatty acids derived from fish oils are injected in incremental portions into the resulting urea solution and cooled to room temperature at the rate of 0.20° C.~0.50° C./min.;

(2) after the step of the first urea-addition crystallization, the step of removing the saturated and unsaturated fatty acids in the form of urea inclusion compound by filtration under reduced pressure;

(3) step of evaporating the filtrate containing the unsaturated fatty acid thus obtained using a vacuum rotary evaporator to remove the residual methanol thereby obtaining the solid product;

(4) step of adding water and a small amount of hydrochloric acid to the solid product and then stirring the mixture to remove any trace amount of the residual urea and methanol in the solid product thereby recovering the upper layer containing the unsaturated fatty acid;

(5) step of the second urea-addition crystallization wherein urea is added to methanol in the weight ratio of methanol: urea=2.5~3.2:1~2 and completely dissolved at elevated temperature of 65° C. to 75° C., and then the fatty acids separated from the step (4) are injected in incremental portions over 5 to 8 steps into the resulting urea solution and cooled to room temperature at the rate of 0.2° C.~0.5° C./mm;

(6) step of filtering the mixture under reduced pressure to remove the filtrate containing impurities and recover the concentrated EPA as the urea inclusion compound in the form of a solid particle;

(7) step of adding water and hexane to the unsaturated fatty acid thus recovered in the form of a solid particle and then adding a small amount of hydrochloric acid to cause the phase separation of urea and concentrated EPA thereby recovering EPA having a high purity as the upper layer;

(8) step of washing the resulting concentrated EPA 2 to 3 times with water and then removing hexane using a rotary evaporator to obtain EPA having a high purity; and (9) step of passing high-purified EPA obtained in the step (8) through a high liquid chromatography column filled with Ag-silica or Ag-alumina.

* * * * *

UNITED STATES PATENT AND TRADEMARK OFFICE

CERTIFICATE OF CORRECTION

PATENT NO. : 6,664,405 B2 
DATED : December 16, 2003
INVENTOR(S) : Seong Kweon Lee It is certified that error appears in the above-identified patent and that said Letters Patent is hereby corrected as shown below:

Title page,
Item [75], Inventors, "(KR)" should read -- (KR); Hee Do Kim, Ansan (KR) --

Signed and Sealed this

Thirtieth Day of March, 2004

JON W. DUDAS
*Acting Director of the United States Patent and Trademark Office*